(12) United States Patent
Morrison et al.

(10) Patent No.: US 11,253,461 B2
(45) Date of Patent: Feb. 22, 2022

(54) MATTE NAIL COMPOSITIONS CONTAINING POLYLACTIC ACID MICROPARTICLES

(71) Applicant: L'ORÉAL, Paris (FR)

(72) Inventors: Sam B. Morrison, Clark, NJ (US); Ramakrishnan Hariharan, Springfield, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 15/797,810

(22) Filed: Oct. 30, 2017

(65) Prior Publication Data

US 2019/0125653 A1    May 2, 2019

(51) Int. Cl.
| | | |
|---|---|---|
| *A61K 8/85* | (2006.01) | |
| *A61Q 3/02* | (2006.01) | |
| *A61K 8/02* | (2006.01) | |

(52) U.S. Cl.
CPC .............. *A61K 8/85* (2013.01); *A61K 8/0241* (2013.01); *A61K 8/0245* (2013.01); *A61Q 3/02* (2013.01); *A61K 2800/26* (2013.01); *A61K 2800/31* (2013.01); *A61K 2800/884* (2013.01)

(58) Field of Classification Search
CPC .... A61K 8/85; A61K 8/0245; A61K 2800/26; A61K 2800/884; A61K 8/0241; A61K 2800/31; A61Q 3/02
See application file for complete search history.

(56) References Cited

U.S. PATENT DOCUMENTS

| | | | |
|---|---|---|---|
| 8,889,107 B2 | 11/2014 | Schmidt et al. | |
| 9,017,812 B2 * | 4/2015 | Takezaki | C08J 3/14 424/502 |
| 2003/0175225 A1 * | 9/2003 | Leacock | A61K 8/29 424/61 |
| 2008/0268002 A1 * | 10/2008 | Dumousseaux | A61K 8/0241 424/401 |
| 2010/0099841 A1 | 4/2010 | Lin | |
| 2011/0287105 A1 * | 11/2011 | Gittleman | A61K 8/046 424/501 |

FOREIGN PATENT DOCUMENTS

| | | | |
|---|---|---|---|
| CN | 105616194 | 6/2016 | |
| WO | WO-0027347 A1 * | 5/2000 | ............... A61K 8/84 |

* cited by examiner

*Primary Examiner* — Quanglong N Truong
(74) *Attorney, Agent, or Firm* — Oblon, McClelland, Maier & Neustadt, L.L.P.

(57) ABSTRACT

The invention relates to matte nail compositions including polylactic acid microparticles, as well as to methods, kits and nail composition sets related to such compositions.

10 Claims, No Drawings

MATTE NAIL COMPOSITIONS CONTAINING POLYLACTIC ACID MICROPARTICLES

FIELD OF THE INVENTION

The present invention relates to matte nail compositions comprising polylactic acid microparticles, as well as to methods of improving matte properties of nail compositions by including polylactic acid microparticles in the nail compositions.

DISCUSSION OF THE BACKGROUND

Traditionally, matte properties have been provided to nail compositions by including silica in the compositions. However, improvements in matte nail compositions, and in ways to provide matte properties to nail compositions, are desired.

Further, previous attempts to use polylactic acid in cosmetics focused on the use of conventional polylactic acid powders.

U.S. Pat. No. 8,889,107 discloses conventional polylactic acid as a biodegradable polymer in micronized form.

US 2010/0099841 discloses compositions having amorphous polylactic acid resin which has been extracted from plants as the main ingredient in the composition to provide for a biodegradable composition.

CN 105616194 discloses compositions in which polylactic acid is one ingredient in a mixture of ingredients that is designed to modify the shrinking tension to create desirable cracking on the surface giving unique visual characteristics.

There remains a need for new ways to improve matte properties in nail compositions.

SUMMARY OF THE INVENTION

The present invention relates to a matte nail composition comprising polylactic acid microparticles.

The present invention also relates to a matte nail composition comprising at least one coloring agent and polylactic acid microparticles.

The present invention also relates to a matte nail composition set comprising at least one color coat comprising at least one coloring agent and at least one topcoat comprising polylactic acid microparticles.

The present invention also relates to a kit comprising at least one color coat composition comprising at least one coloring agent and at least one topcoat comprising polylactic acid microparticles.

The present invention also relates to a matte nail composition set comprising at least one color coat comprising at least one coloring agent and at least one basecoat comprising polylactic acid microparticles.

The present invention also relates to a kit comprising at least one color coat composition comprising at least one coloring agent and at least one basecoat comprising polylactic acid microparticles.

The present invention also relates to methods of improving matte properties of a nail composition comprising adding polylactic acid microparticles to the nail composition during preparation of the nail composition in an amount sufficient to enhance matte properties of the nail composition.

The present invention further relates to methods for making up and/or protecting nails comprising applying to the nails a matte nail composition comprising polylactic acid microparticles.

The present invention further relates to methods for making up and/or protecting nails comprising applying to the nails (1) at least one color coat comprising at least one coloring agent, and (2) at least one topcoat comprising polylactic acid microparticles.

The present invention further relates to methods for making up and/or protecting nails comprising applying to the nails (1) at least one basecoat comprising polylactic acid microparticles; and (2) at least one color coat comprising at least one coloring agent.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means a polymer or resin that leaves a film on the substrate to which it is applied, for example, after a solvent accompanying the film former has evaporated, absorbed into and/or dissipated on the substrate.

"Makeup Result" as used herein, refers to compositions where color remains the same or substantially the same as at the time of application, as viewed by the naked eye, after an extended period of time. "Makeup Result" may be evaluated by evaluating long wear properties by any method known in the art for evaluating such properties. For example, long wear may be evaluated by a test involving the application of a composition to nails and evaluating the color of the composition after an extended period of time. For example, the color of a composition may be evaluated immediately following application to nails and these characteristics may then be re-evaluated and compared after a certain amount of time. Further, these characteristics may be evaluated with respect to other compositions, such as commercially available compositions.

"Adhesion" as used herein, refers to chemical or physical bonding between a coating and a substrate. Good adhesion between nail polish and nail surface should translate to good wear properties on consumers. Adhesion properties can be quantified by in-vitro method such as a cross-cut adhesion test. In the test, a lattice pattern is cut into the coating and penetrates through to the substrate. A pressure sensitive tape is applied to the sample and then pulled off. The adhesion property can be quantified by the area of the coating remaining after peeling. For example, if the whole film remains after peeling, it indicates excellent adhesion. If most of the film gets peeled off, it indicates poor adhesion. The cross-cut test is an industrial standard test for testing adhesion for coatings. (Reference #ISO/DIN 2409, ASTM D3359).

"Substituted" as used herein, means comprising at least one substituent. Non-limiting examples of substituents for substitution include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, and polysiloxane groups. The substituent(s) may be further substituted.

"Nail" as used herein includes fingernails as well as toenails.

"Volatile", as used herein, means having a flash point of less than about 100° C.

"Non-volatile", as used herein, means having a flash point of greater than about 100° C.

"Matte" in compositions as used herein refers to compositions having with average gloss properties, measured at 20°, of less than or equal to 10, for example 9, preferably 8, 6, 5 or 4, including all ranges and subranges therebetween such as 1-10, 1-5, 2-10, 3-8, etc.

The term "average gloss properties" denotes the gloss as it can be measured using a gloss meter, for example by spreading a layer of the composition to be tested, between 50 µm and 150 µm in thickness, on a white Leneta contrast card using an automatic spreader. The deposit is cured under UV-LED lamp for 1 min. The residual tacky layer is wiped off with lint free cotton saturated in alcohol solvent, and then the gloss is measured at 20° using a Byk Gardner gloss meter of reference microTRI-GLOSS. This measurement is repeated at least three times, and the average gloss in GU (gloss units) is the average of the at least three measurements carried out.

The compositions, coats and methods of the present invention can comprise, consist of, or consist essentially of the essential elements and limitations of the invention described herein, as well as any additional or optional ingredients, components, or limitations described herein or otherwise useful. For example, the compositions and coats can "consist essentially of" or "consist of" polylactic acid microparticles as a mattifying agent.

The compositions and methods of the present invention can "comprise," "consist of" or "consist essentially of" the essential elements and limitations of the invention described herein, as well as any additional or optional ingredients, components, or limitations described herein or otherwise useful. For purposes of the compositions and methods of the present invention where the invention "consists essentially of" the identified ingredients and/or process steps, the sole "basic and novel property" of such compositions and/or methods is "matte." Further, given that it is contemplated that other mattifying agents can be added to the invention methods and compositions in the context of the present invention, a "material effect" on the basic and novel property of the invention can only be an adverse effect. That is, because positive effects on matte properties (such as those effected by mattifying agents such as silica) are within the scope of the present invention, only ingredients which have a material adverse effect on matte properties provided by the polylactic acid microparticles would be relevant to determining whether or not compositions or methods "consist essentially of" the required elements.

Matte Nail Composition

According to the present invention, a matte nail composition comprising polylactic acid microparticles is provided.

Polylactic Acid Microparticles

According to preferred embodiments of the present invention, the polylactic acid microparticles are those described in U.S. Pat. No. 8,968,787 and/or U.S. Pat. No. 9,017,812, the entire disclosures of which are hereby incorporated by reference. The polylactic acid microparticles can contain D- and/or L-lactic acid, meaning that the microparticles can be made from copolymers in which main components are L-lactic acid and/or D-lactic acid such that, in the monomer units constituting copolymers, the total of the monomer units of L-lactic acid and D-lactic acid are 50 mole % or more in the molar ratio. The molar ratio of the total of the monomer units of L-lactic acid and D-lactic acid is preferably 50 mole % or more, preferably 70 mole % or more, preferably 80 mole % or more, and preferably 90 mole % or more, with the upper limit being 100 mole %. "L" and "D" refer to kinds of optical isomers. The lactic acid having a native type configuration is described as "L-lactic acid" or "L-type lactic acid," and the lactic acid having a non-native type configuration is described as "D-lactic acid" or "D-type lactic acid."

Preferably, the polylactic acid microparticles have a number average particle diameter smaller than about 100 microns, preferably smaller than about 80 microns, preferably smaller than about 60 microns, preferably smaller than about 50 microns, preferably smaller than about 30 microns and preferably larger than about 1 micron, preferably larger than about 2 microns, preferably larger than about 3 microns and preferably larger than about 5 microns, including all ranges and subranges therebetween. Examples of acceptable polylactic acid microparticles are commercially available from Toray Industries under the trade name of TORAYPEARL™ such as, for example, TORAYPEARL™ PLA (a porous particle having a size of about 11 µm).

The polylactic acid microparticles preferably have a porous surface.

Regarding the particle diameter distribution of the polylactic acid microparticles, the particle diameter distribution index is preferably 2 or less, preferably 1.5 or less, preferably 1.3 or less, and preferably 1.2 or less, with calculations capable of being performed as described in U.S. Pat. No. 9,017,812.

The above-described number average particle diameter can be calculated by measuring diameters of 100 random particles in a scanning electron microscope image and computing the arithmetic average thereof. If a shape of a particle in the SEM image is not a perfect circle, for example, an ellipse, the maximum diameter of the particle is used as its diameter. To measure the particle diameter precisely, the measurement is carried out with a magnification of at least 1000 times or more, preferably 5000 times or more.

Although porosity (actual amount of pores in a porous microparticle) can be difficult to measure directly, it is possible to use linseed oil absorption capacity as an indirect index, which is defined in pigment test methods such as Japan Industrial Standards (Refined Linseed Oil Method, JIS K 5101). Preferably, the polylactic acid microparticles of the present invention have linseed oil absorption capability of 90 ml/100 g or more, preferably 100 ml/100 g or more, preferably 120 ml/100 g or more, preferably 150 ml/100 g or more, preferably 200 ml/100 g or more, and preferably 300 ml/100 g or more, with an upper limit of linseed oil absorption capability of preferably 1000 ml/100 g or less, including all ranges and subranges therebetween.

Further, it is preferred that the polylactic acid microparticles have enthalpy of fusion of 5 J/g or more, preferably 10 J/g or more, preferably 20 J/g or more, and preferably 30 J/g or more, with the upper limit preferably being 100 J/g or less, including all ranges and subranges therebetween, with calculations capable of being performed as described in U.S. Pat. No. 9,017,812.

Preferably, the polylactic acid microparticles have a sphericity of 80 or more, preferably 85 or more, preferably 90 or more, preferably 92 or more, and preferably 95 or more, with the upper limit being 100, including all ranges and subranges therebetween, with sphericity calculations capable of being performed as described in U.S. Pat. No. 9,017,812.

In accordance with preferred embodiments, the polylactic acid microparticles are preferably present in the nail compositions in an amount sufficient to impart matte properties to the composition.

For a nail composition comprising a coloring-effective amount of at least one coloring agent, the polylactic acid microparticles are preferably present in the nail composition in an amount of active material from about 0.1% to about 3% by weight, preferably from about 0.25% to about 2.5% by weight, preferably from about 0.33% to about 2%, and preferably from about 0.75% to about 2% by weight of the total weight of the composition, including all ranges and subranges therebetween.

For a nail composition which does not comprise a coloring-effective amount of at least one coloring agent (for example, a topcoat which does not contain coloring agent), the polylactic acid microparticles are preferably present in the nail composition in an amount of active material from about 0.1% to about 5% by weight, preferably from about 0.15% to about 4% by weight, preferably from about 2% to about 4% by weight, and preferably from about 0.2% to about 3% by weight of the total weight of the composition, including all ranges and subranges therebetween.

"Active material" in this context means polylactic acid microparticles themselves, so, for example, an aqueous dispersion of polylactic acid microparticles contains water and a certain amount of polylactic acid microparticles (depending upon the dispersion), but only the polylactic acid microparticles are "active material" in this dispersion.

Other Ingredients

According to the present invention, a matte nail composition comprising at least one other ingredient typically found in nail compositions is provided. One of ordinary skill in the art would readily understand the types of ingredients typically found in nail compositions. A non-exhaustive list of such ingredients includes, but is not limited to, cellulose compounds, film forming agents, plasticizing agents, coalescing agents, and coloring agents.

Suitable cellulose compounds include, but are not limited to, cellulose polymers, such as, for example, hydroxyethylcellulose, hydroxypropylcellulose, methylcellulose, ethylhydroxyethylcellulose and nitrocellulose.

According to preferred embodiments, the at least one cellulose compound, if present, is present in the compositions of the present invention in an amount of active material ranging from about 0.01 to about 30% by weight, more preferably from about 0.1 to about 20% by weight, and most preferably from about 1 to about 10% by weight, based on the total weight of the composition, including all ranges and subranges within these ranges.

Suitable film forming agents include water-soluble film forming agents and oil-soluble film forming agents.

Specific examples of suitable water-soluble film forming agents include, but are not limited to, latexes, proteins, such as proteins of plant origin, such as, for example, wheat or soya proteins; or proteins of animal origin, such as keratins, for example keratin hydrolysates and sulfonic keratins; acrylic polymers or copolymers, such as, for example, polyacrylates or polymethacrylates; vinyl polymers, such as, for example, polyvinylpyrrolidones, copolymers of methyl vinyl ether and of maleic anhydride, the copolymer of vinyl acetate and of crotonic acid, copolymers of vinylpyrrolidone and of vinyl acetate, copolymers of vinylpyrrolidone and of caprolactam, or polyvinyl alcohol; gums arabic, guar gum, xanthan derivatives or karaya gum; alginates and carrageenans; glycoaminoglycans, hyaluronic acid and its derivatives; shellac resin, gum sandarac, dammars, elemis or copals; muccopolysaccharides, such as chondroitin sulfates; and their mixtures.

According to preferred embodiments, the at least one film forming agent, if present, is present in the compositions of the present invention in an amount of active material ranging from about 0.01 to about 30% by weight, more preferably from about 0.1 to about 20% by weight, and most preferably from about 1 to about 10% by weight, based on the total weight of the composition, including all ranges and subranges within these ranges.

Plasticizers (plasticizing agents) are additives used to optimize the mechanical properties of the films. They tend to reduce the Glass Transition Temperature (Tg) and increase the softness and flexibility of the films. Preferably, the plasticizer has a distribution coefficient D of less than or equal to 0.1. The distribution coefficient can be determined in accordance with the teaching of "A method to predict the distribution coefficient of coalescing agents between latex particles and the water phase," *Progress in Organic Coatings*, vol. 30, 1997, pp. 173-177, the disclosure of which is specifically incorporated by reference herein.

Preferably, the plasticizer has a boiling point measured at ambient pressure of less than or equal to 285° C., preferably less than or equal to 270° C., and preferably less than or equal to 250° C. In the present specification, the boiling point values are to be considered accurate to ±2° C. owing to the uncertainties of boiling point measurement.

Any plasticizing agent typically found in nail polish compositions can be used. Examples of suitable plasticizers include, but are not limited to, glycols and their ester derivatives, esters of acids, in particular carboxylic acids, such as citrates, adipates, carbonates, tartrates, phosphates or sebacates, oxyethylenated derivatives, such as oxyethylenated oils, and their mixtures. For example, suitable plasticizing agents include, but are not limited to, diisobutyl adipate, the ester of teributyl acid and 2,2,4-trimethylpentane-1,3-diol, diethyl adipate, diethyl phthalate, dibutyl phthalate, dioctyl phthalate, butyl 2-ethylhexyl phthalate, dimethyl sebacate, dibutyl sebacate, ethyl stearate, 2-ethylhexyl palmitate, dipropylene glycol n-butyl ether, tributyl phosphate, tributoxyethyl phosphate, tricresyl phosphate, triphenyl phosphate, glycerol triacetate, butyl stearate, butyl glycolate, benzyl benzoate, butyl acetyltricinoleate, glyceryl acetyltricinoleate, dibutyl phthalate, diisobutyl phthalate, dioctyl phthalate, dimethoxyethyl phthalate, diamyl phthalate, triethyl citrate, tributyl citrate, tributyl acetylcitrate, tri(2-ethylhexyl) acetylcitrate, dibutyl tartrate, camphor, and mixtures thereof.

In accordance with preferred embodiments, the plasticizer, if present, is preferably present in the primer composition in an amount of from 0.1% to 25% by weight, preferably from 0.25% to 22% by weight, preferably from 0.5 to 20% by weight, of the total weight of the composition, including all ranges and subranges therebetween.

Coalescents (coalescing agents) are additives used assist the film formation process of certain film forming agents (e.g., latex). Preferably, the coalescent agent has a distribution coefficient D' of greater than or equal to 0.5, measured in accordance with the above-referenced "A method to predict the distribution coefficient of coalescing agents between latex particles and the water phase," *Progress in Organic Coatings*, vol. 30, 1997, pp. 173-177. Preferably, the coalescent agent has a boiling point measured at ambient pressure ranging from 90° C. to 180° C., preferably from 150° C. to 180° C.

Any coalescent agent typically found in nail polish compositions can be used. Examples of suitable plasticizers include, but are not limited to, propylene glycol n-butyl ether, dipropylene glycol dimethyl ether, propylene glycol methyl ether acetate, propylene glycol propyl ether, methyl lactate, ethyl lactate, isopropyl lactate, and mixtures thereof.

In accordance with preferred embodiments, the coalescent agent, if present, is preferably present in the primer composition in an amount of from 0.1% to 25% by weight, preferably from 1% to 15% by weight, preferably from 3 to 10% by weight, of the total weight of the composition, including all ranges and subranges therebetween.

Suitable colorants (coloring agents) include any colorant typically found in nail compositions. Suitable colorants include, but are not limited to, lipophilic dyes, pigments and pearlescent agents, and their mixtures.

Suitable examples of fat-soluble dyes are, for example, Sudan red, DC Red 17, DC Green 6, β-carotene, soybean oil, Sudan brown, DC Yellow 11, DC Violet 2, DC Orange 5 and quinoline yellow.

Suitable pigments can be white or colored, inorganic and/or organic and coated or uncoated. Mention may be made, for example, of inorganic pigments such as titanium dioxide, optionally surface treated, zirconium or cerium oxides and iron or chromium oxides, manganese violet, ultramarine blue, chromium hydrate and ferric blue. Mention may also be made, among organic pigments, of carbon black, pigments of D & C type and lakes based on cochineal carmine or on barium, strontium, calcium or aluminum, such as D&C Red No. 10, 11, 12, and 13, D&C Red No. 7, D&C Red No. 5 and 6, and D&D Red No. 34, as well as lakes such as D&C Yellow Lake No. 5 and D&C Red Lake No. 2.

Suitable pearlescent pigments can be chosen from, for example, white pearlescent pigments, such as mica covered with titanium oxide or with bismuth oxychloride, colored pearlescent pigments, such as titanium oxide-coated mica with iron oxides, titanium oxide-coated mica with in particular ferric blue or chromium oxide, or titanium oxide-coated mica with an organic pigment of the abovementioned type, and pearlescent pigments based on bismuth oxychloride.

In accordance with preferred embodiments of nail compositions providing color to a nail, the colorant is preferably present in an amount sufficient to provide color to the nail, preferably in an amount of from about 0.1% to about 20% by weight, preferably from about 0.25% to about 15% by weight, and preferably from about 0.5 to about 10% by weight, of the total weight of the composition, including all ranges and subranges therebetween.

Nail Composition Set

According to the present invention, matte nail composition sets comprising (1) at least one color coat comprising at least one coloring agent and (2) at least one basecoat comprising polylactic acid microparticles and/or at least one topcoat comprising polylactic acid microparticles are provided.

According to preferred embodiments, the basecoat and/or topcoat of the matte nail composition has a smooth appearance (that is, visual cracks do not appear) on the nail.

For example, a matte nail composition set comprising at least one basecoat, at least one color coat and at least one topcoat are provided. However, the basecoat or topcoat are optional. Thus, matte nail composition sets comprising at least one color coat and at least one top coat, as well as matte nail composition sets comprising at least one basecoat and at least one color coat are provided by the present invention.

It should be understood that each coat or layer in the matte nail composition set, itself, can comprise one or more layers of each composition. Thus, the at least one basecoat can comprise one or more basecoat layers; the at least one color coat can comprise one or more color coat layers; and the at least one topcoat can comprise one or more topcoat layers. Preferably, each basecoat, color coat and topcoat contains three or fewer layers or compositions, more preferably two or fewer layers or compositions, and most preferably a single layer or composition.

According to the present invention, the basecoat, color coat and topcoat of the matte nail composition set can be any suitable composition for application to nails. For example, the basecoat(s) can be an adhesive layer or an undercoat layer; and the topcoat(s) can be a protective layer. The color coat(s) can be a UV gel nail composition or a conventional nail composition, if desired.

Examples of suitable UV gel nail compositions can be found, for example, in U.S. Pat. Nos. 5,435,994, and 5,456,905, and US patent application publication nos. 2011/082228, 2011/081306, 2011/060065, 2011/182838, 2011/274633. Further, suitable compositions can be found in U.S. Ser. No. 61/476,339, the entire contents of which is hereby incorporated by reference in its entirety.

Examples of suitable conventional solvent-based compositions can be found, for example, in U.S. Pat. Nos. 7,455,831, 7,025,953, 6,555,096, 6,372,201, 6,333,025, and 6,254,878, the entire contents of all of which are hereby incorporated by reference in their entireties.

During application of the matte nail composition set, the basecoat (if used) is applied to the nail. The color coat is applied to the basecoat (if used); if basecoat is not used, the color coat is applied to the nail. Then, if used, the topcoat is applied to the color coat. In this manner, a matte nail composition set comprising a basecoat (optional), a color coat and a topcoat (optional) can be prepared on a nail.

Auxiliaries/Additives

The compositions discussed above may additionally comprise an additive or auxiliary commonly used in cosmetic compositions and known to a person skilled in the art as being capable of being incorporated into a nail polish or varnish composition. Such additives or auxiliaries may be chosen from solvents, thickeners, coalescents, preservatives, fragrances, oils, waxes, surfactants, antioxidants, agents for combating free radicals, spreading agents, wetting agents, dispersing agents, antifoaming agents, neutralizing agents, stabilizing agents, active principles chosen from essential oils, UV screening agents, sunscreens, moisturizing agents, vitamins, proteins, ceramides, plant extracts, fibers, and the like, and their mixtures.

A person skilled in the art will take care to select the optional additional additives and/or the amount thereof such that the advantageous properties of the compositions according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Needless to say, the compositions of the invention should be cosmetically or dermatologically acceptable, i.e., they should contain a non-toxic physiologically acceptable. The compositions may be in any galenic form normally employed in the cosmetic and dermatological fields which is suitable for topical administration onto nails.

According to preferred embodiments, compositions of the invention comprise at least one organic solvent. Suitable examples of solvents, include, but are not limited to, ketones which are liquid at room temperature such as, for example, methyl ethyl ketone, methyl isobutyl ketone, diisobutyl ketone, isophorone, cyclohexanone, and acetone; alcohols which are liquid at room temperature, such as ethanol, isopropanol, n-propanol, n-butanol, diacetone alcohol, 2-butoxyethanol, and cyclohexanol; glycols which are liquid at room temperature, such as ethylene glycol, propylene glycol, pentylene glycol, and glycerol; propylene glycol ethers which are liquid at room temperature, such as propylene glycol monomethyl ether, propylene glycol monomethyl ether acetate, and dipropylene glycol mono-n-butyl ether; short-chain esters (having from 3 to 8 carbon atoms in total) such as ethyl acetate, methyl acetate, propyl acetate, n-butyl acetate, and isopentyl acetate; ethers which are liquid at room temperature, such as diethyl ether, dimethyl ether, and dichlorodiethyl ether; alkanes which are liquid at room temperature such as decane, heptane, dodecane, isododecane, and cyclohexane; aromatic cyclic compounds which are liquid at room temperature, such as toluene and xylene; and aldehydes which are liquid at room temperature, such as benzaldehyde and acetaldehyde. If present, the organic solvent preferably comprises from about 10% to about 95% by weight, preferably from about 30% to about 90% by weight, and preferably from about 50% to about 85% by weight, relative to the total weight of the composition.

According to preferred embodiments, the compositions of the present invention are substantially free of water (i.e., contain less than about 1% water). In other embodiments, the compositions are free of water (i.e., contain less than about 0.1% water).

According to preferred embodiments of the present invention, methods for making up and/or protecting nails comprising applying to the nails (1) at least one basecoat comprising polylactic acid microparticles; and (2) at least one color coat comprising at least one coloring agent are provided.

According to preferred embodiments of the present invention, methods for making up and/or protecting nails comprising applying to the nails (1) at least one color coat comprising at least one coloring agent, and (2) at least one topcoat comprising polylactic acid microparticles are provided.

"Making up" as used herein means to provide decoration (for example, color) to the nail. "Protecting" as used herein means to inhibit damage to the nail (for example, chipping) by providing a protective layer on the nail.

In accordance with preferred embodiments of the preceding methods, at least one color coat is applied topically to the nails of a person in need of (desirous) the desired making up or protection in an amount sufficient to achieve the desired result. The coats may be applied to the desired area as needed.

According to preferred embodiments of the present invention, a kit comprising (1) at least one basecoat composition comprising polylactic acid microparticles; and (2) at least one color coat composition comprising at least one coloring agent is provided.

According to preferred embodiments of the present invention, a kit comprising (1) at least one color coat composition comprising at least one coloring agent, and (2) at least one topcoat composition comprising polylactic acid microparticles is provided.

The compositions according to the invention can be manufactured by known processes used generally in the cosmetics or dermatological field.

According to preferred embodiments of the present invention, methods of improving matte properties of a nail composition comprising adding polylactic acid microparticles to the nail composition during preparation of the nail composition in an amount sufficient to enhance matte properties of the nail composition are provided.

Preferably, sufficient polylactic acid microparticles are added to the nail composition to provide the composition with average gloss properties, measured at 20°, of less than or equal to 10, preferably less than or equal to 9, 8, 6, 5 or 4, including all ranges and subranges therebetween such as 1-10, 1-5, 2-10, 3-8, etc.

Preferably, sufficient polylactic acid microparticles are added to the nail composition to provide the composition with average gloss properties, measured at 20°, which is greater than 80% lower than the average gloss properties of the nail composition without the polylactic acid microparticles, preferably greater than 85%, preferably greater than 90% and preferably greater than 95% (so, for example, a nail composition without polylactic acid microparticles having an average gloss of 50 which has its average gloss lowered to 5 after addition of polylactic acid particles corresponds to a gloss value which is 90% lower).

Generally speaking, for a nail composition comprising a coloring-effective amount of at least one coloring agent, the polylactic acid microparticles are preferably added to the nail composition in an amount of active material from about 0.1% to about 3% by weight, preferably from about 0.15% to about 2.5% by weight, and preferably from about 0.2% to about 2% by weight of the total weight of the composition, including all ranges and subranges therebetween. For a nail composition which does not comprise a coloring-effective amount of at least one coloring agent (for example, a topcoat which does not contain coloring agent), the polylactic acid microparticles are preferably added to the nail composition in an amount of active material from about 0.1% to about 5% by weight, preferably from about 0.15% to about 4% by weight, and preferably from about 0.2% to about 3% by weight of the total weight of the composition, including all ranges and subranges therebetween.

According to preferred embodiments of the present invention, methods of improving matte properties of a nail composition set comprising adding polylactic acid microparticles to a topcoat or basecoat during preparation of the topcoat composition or basecoat composition in an amount sufficient to enhance matte properties of the nail composition set are provided.

Preferably, sufficient polylactic acid microparticles are added to the topcoat composition or basecoat composition to provide the nail composition set with average gloss properties, measured at 20°, of less than or equal to 10, preferably less than or equal to 9, 8, 6, 5 or 4, including all ranges and subranges therebetween such as 1-10, 1-5, 2-10, 3-8, etc.

Preferably, sufficient polylactic acid microparticles are added to the topcoat composition or basecoat composition to provide the nail composition set with average gloss properties, measured at 20°, which is greater than 80% lower than the average gloss properties of the nail composition set without the polylactic acid microparticles, preferably greater than 85%, preferably greater than 90% and preferably greater than 95% (so, for example, a nail composition set without polylactic acid microparticles having an average gloss of 50 which has its average gloss lowered to 5 after addition of polylactic acid particles corresponds to a gloss value which is 90% lower).

Generally speaking, for a topcoat composition or basecoat composition, the polylactic acid microparticles are preferably added to the composition in an amount of active material from about 0.1% to about 5% by weight, preferably from about 0.15% to about 4% by weight, and preferably from about 0.2% to about 3% by weight of the total weight of the composition, including all ranges and subranges therebetween.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

EXAMPLES

Example 1: Color Coat Containing Coloring Agent And Polylactic Acid Microparticles The following compositions were prepared:

| INCI US | Example 1 |
| --- | --- |
| CITRIC ACID | 0.04 |
| POLYLACTIC ACID | 0.5 |
| HYDROGENATED ACETOPHENONE/OXYMETHYLENE COPOLYMER | 0.26 |
| ROSIN | 0.02 |
| ETHYL TOSYLAMIDE | 2.65 |
| PROPYL ACETATE/BUTYL ACETATE/ETHYL ACETATE | 63 |
| TITANIUM DIOXIDE | 1.73 |
| COLORANT | 0.41 |
| ACRYLATES COPOLYMER | 1.12 |
| ADIPIC ACID/NEOPENTYL GLYCOL/TRIMELLITIC ANHYDRIDE COPOLYMER | 0.30 |
| UVB SUNSCREEN | 0.54 |
| SILICONE OIL | 0.1 |
| ISOPROPYL ALCOHOL | 6.57 |
| OXIDIZED POLYETHYLENE | 0.05 |
| BARIUM SULFATE | 0.13 |
| ACETYL TRIBUTYL CITRATE/TRIBUTYL CITRATE | 3.95 |
| CELLULOSE FILM FORMER | 9.65 |
| STEARALKONIUM HECTORITE | 1.03 |
| TOSYLAMIDE/EPOXY RESIN | 7.97 |

Example 2: Topcoat Containing Polylactic Acid Microparticles

| INCI US | Example 2 |
| --- | --- |
| ACETYL TRIBUTYL CITRATE/TRIBUTYL CITRATE | 6.45 |
| CITRIC ACID | 0.03 |
| STEARALKONIUM HECTORITE | 0.86 |
| NITROCELLULOSE (and) ISOPROPYL ALCOHOL | 16.22 |
| ADIPIC ACID/NEOPENTYL GLYCOL/TRIMELLITIC ANHYDRIDE COPOLYMER | 5.16 |
| BUTYL ACETATE (and) ACRYLATES COPOLYMER | 1.29 |
| POLYLACTIC ACID | 4 |
| BUTYL ACETATE/ETHYL ACETATE | 64.55 |
| UVB SUNSCREEN | 0.43 |

Example 3: Comparative Testing

The following compositions were prepared:

| Chemical Name | Comparative Example 1 | Example 3A | Example 3B | Example 3C | Example 3RT |
| --- | --- | --- | --- | --- | --- |
| Primary Film Former (Nitrocellulose - 70% active material in solvent) | 16.23 | 16.11 | 15.99 | 15.91 | 15.91 |

-continued

| Chemical Name | Comparative Example 1 | Example 3A | Example 3B | Example 3C | Example 3RT |
|---|---|---|---|---|---|
| Secondary Film Former (Polyester, Epoxy Resin, Acrylate and Polyol) | 13.16 | 13.06 | 12.96 | 12.89 | 12.89 |
| Plasticizer (TBC, ATBC) | 5.42 | 5.37 | 5.32 | 5.28 | 5.28 |
| Solvents (IPA, EA, PA and BA) | 63.41 | 62.93 | 62.46 | 62.14 | 62.14 |
| Others (Benzophenone, Stearalkonium Hectorite and silica) | 1.43 | 1.42 | 1.42 | 1.42 | 1.42 |
| Pigments (iron oxides and titanium dioxide) | 0.36 | 0.36 | 0.36 | 0.36 | 0.36 |
| Polylactic Acid | 0.00 | 0.75 | 1.50 | 2.00 | 2.00 |
|  | 100.00 | 100.00 | 100.00 | 100.00 | 100.00 |

The above compositions were similar except with respect to mattifying agent(s) present. One composition did not contain polylactic acid (PLA) microparticles. The remaining compositions contained varying amounts of PLA (0.75%, 1.50% and 2%). The gloss of all compositions was measured to determine the mattifying effect of PLA.

Another composition representative of more conventional nail compositions containing 2% silica (Comparative Example 2) was also prepared and tested.

Gloss of the compositions was determined as follows: Films were drawn down onto Laneta Form 5C—Opacity cards and allowed to dry. Gloss measurements were made using a BYK micro-TRI-gloss meter at the 20° reflectance angle.

Results: As demonstrated in the chart below, the experiment demonstrated that addition of PLA resulted in a mattfying effect. Gloss readings became lower when PLA concentrations were increased, indicating that gloss is reduced and a greater matte effect is achieved at higher PLA concentrations.

| Formula | PLA (%) | Gloss @ 20° |
|---|---|---|
| Comparative Example 1 | 0 | 38.7 |
| Example 3A | 0.75 | 3.5 |
| Example 3B | 1.50 | 1.3 |
| Example 3C | 2 | 0.6 |
| Comparative Example 2 (containing 2% silica) | 0 | 1.1 |

What is claimed is:

1. A nail composition kit, comprising:
   (a) at least one color coat comprising at least one coloring agent; and
   (b) at least one basecoat comprising polylactic acid microparticles and/or at least one topcoat comprising polylactic acid microparticles, wherein the basecoat and/or topcoat is/are a nail composition having average gloss properties, measured at 20°, of less than or equal to 10 and wherein the polylactic acid microparticles have a number average particle diameter of 1 to 30 microns,
   wherein the nail composition further comprises at least one organic solvent in an amount of from about 10% to about 95% by weight relative to the total weight of the nail composition and at least one compound selected from the group consisting of cellulose compounds, film forming agents, and mixtures thereof,
   and wherein
      if the nail composition comprises a coloring-effective amount of a coloring agent, the polylactic acid microparticles are present in an amount of 0.1 to 3% by weight, relative to the total weight of the composition, and
      if the nail composition does not comprise a coloring-effective amount of a coloring agent, the polylactic acid microparticles are present in an amount of 0.1 to 5% by weight, relative to the total weight of the nail composition.

2. The nail composition kit of claim 1, wherein the nail composition has average gloss properties, measured at 20°, of less than or equal to 5.

3. The nail composition kit of claim 1, wherein the nail composition has average gloss properties, measured at 20°, of less than or equal to 3.

4. The nail composition kit of claim 1, wherein the nail composition further comprises at least one coloring agent.

5. The nail composition kit of claim 4, wherein the at least one coloring agent is present in the composition in an amount ranging from 0.1% to 20% by weight with respect to the total weight of the nail composition.

6. The nail composition kit of claim 1, wherein the nail composition is a topcoat composition which comprises from about 0.1% to about 5% by weight of the total weight of the nail composition of polylactic acid microparticles, and does not comprise a coloring-effective amount of a coloring agent.

7. The nail composition kit of claim 1, wherein the polylactic acid microparticles have linseed oil absorption capability of 90 ml/100 g or more.

8. The nail composition kit of claim 1, wherein the polylactic acid microparticles have a particle diameter distribution index of 2 or less.

9. The nail composition kit of claim 1, wherein the nail composition comprises 0.1 to 25% by weight with respect to the weight of the nail composition of at least one plasticizer selected from the group consisting of acetyl tributyl citrate and tributyl citrate.

10. The nail composition kit of claim 9, wherein the nail composition comprises at least one film forming agent which is a tosylamide/epoxy resin.

* * * * *